United States Patent
Lechner et al.

(10) Patent No.: US 11,291,622 B2
(45) Date of Patent: Apr. 5, 2022

(54) METHOD FOR DYEING KERATINOUS MATERIAL, COMPRISING THE USE OF AN ORGANOSILICON COMPOUND, A DYEING COMPOUND AND A SILICON OIL

(71) Applicant: Henkel AG & Co. KGaA, Duesseldorf (DE)

(72) Inventors: Torsten Lechner, Langenfeld (DE); Juergen Schoepgens, Schwalmtal (DE); Marc Nowottny, Moenchengladbach (DE); Gabriele Weser, Neuss (DE); Ulrike Schumacher, Duesseldorf (DE); Claudia Kolonko, Remscheid (DE); Caroline Kriener, Duesseldorf (DE); Carsten Mathiaszyk, Essen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/267,664

(22) PCT Filed: Aug. 7, 2019

(86) PCT No.: PCT/EP2019/071179
§ 371 (c)(1),
(2) Date: Feb. 10, 2021

(87) PCT Pub. No.: WO2020/035359
PCT Pub. Date: Feb. 20, 2020

(65) Prior Publication Data
US 2021/0196616 A1  Jul. 1, 2021

(30) Foreign Application Priority Data
Aug. 16, 2018 (DE) ..................... 10 2018 213 811.7

(51) Int. Cl.
*A61Q 5/10* (2006.01)
*A61K 8/891* (2006.01)
*A61K 8/26* (2006.01)
*A61K 8/58* (2006.01)

(52) U.S. Cl.
CPC .............. *A61K 8/891* (2013.01); *A61K 8/26* (2013.01); *A61K 8/585* (2013.01); *A61Q 5/10* (2013.01); *A61K 2800/4324* (2013.01); *A61K 2800/884* (2013.01); *A61K 2800/95* (2013.01)

(58) Field of Classification Search
CPC .............. A61Q 5/10; A61K 2800/4324; A61K 2800/884; A61K 8/898; A61K 2800/43; A61K 8/25; A61K 8/585; A61K 2800/594; A61K 2800/432; A61K 8/89; A61K 8/891
USPC ............................................................ 8/405
See application file for complete search history.

(56) References Cited

U.S. PATENT DOCUMENTS

| | | | |
|---|---|---|---|
| 7,806,941 B2 | 10/2010 | Brun et al. | |
| 2010/0083446 A1* | 4/2010 | Brun ...................... | A61Q 5/004 8/405 |
| 2014/0076346 A1* | 3/2014 | Bourdin ................... | A61Q 5/12 132/202 |
| 2014/0314696 A1 | 10/2014 | Kergosien et al. | |
| 2016/0184214 A1* | 6/2016 | Bernet ................... | A61K 8/895 424/49 |
| 2016/0235655 A1 | 8/2016 | Herrlein et al. | |
| 2016/0331673 A1* | 11/2016 | Ferritto ................... | C08L 83/04 |
| 2017/0157002 A1* | 6/2017 | Neuba ...................... | A61K 8/19 |

FOREIGN PATENT DOCUMENTS

| | | | |
|---|---|---|---|
| EP | 2168633 | A2 | 3/2010 |
| FR | 2922759 | A1 | 5/2009 |
| FR | 2929112 | A1 | 10/2009 |
| WO | 2013068967 | A2 | 5/2013 |
| WO | 2018115059 | A1 | 6/2018 |

OTHER PUBLICATIONS

EPO, International Search Report issued in International Application No. PCT/EP2019/071179, dated Nov. 13, 2019.

* cited by examiner

*Primary Examiner* — Eisa B Elhilo
(74) *Attorney, Agent, or Firm* — Lorenz & Kopf, LLP

(57) ABSTRACT

The subject of the present disclosure is a process for dyeing keratinous material, in particular human hair. In one example, the process includes applying an agent (a) to the keratinous material. The agent (a) includes at least one organic silicon compound. An agent (b) is applied to the keratinous material. The agent (b) includes at least one colorant compound selected from the group including pigments and/or direct dyes. An agent (c) is applied to the keratinous material. The agent (c) includes at least one silicone oil.

19 Claims, No Drawings

METHOD FOR DYEING KERATINOUS MATERIAL, COMPRISING THE USE OF AN ORGANOSILICON COMPOUND, A DYEING COMPOUND AND A SILICON OIL

CROSS-REFERENCE TO RELATED APPLICATION

This application is a U.S. National-Stage entry under 35 U.S.C. § 371 based on International Application No. PCT/EP2019/071179, filed Aug. 7, 2019, which was published under PCT Article 21(2) and which claims priority to German Application No. 10 2018 213 811.7, filed Aug. 16, 2018, which are all hereby incorporated in their entirety by reference.

TECHNICAL FIELD

The subject of the present application is a process for dyeing keratinous material, especially human hair, which comprises the application of three different agents (a), (b) and (c). The agent (a) contains at least one organic silicon compound. The agent (b) comprises at least one colorant compound selected from the group including pigments and/or direct dyes. The agent (c) is exemplified by its content of at least one silicone oil.

A second subject of this application is a multi-component packaging unit (kit-of-parts) for dyeing keratinous material, in particular human hair, which comprises means (a), (b) and (c) separately assembled in three different containers.

BACKGROUND

Changing the shape and color of keratinous material, especially human hair, is an important area of modern cosmetics. To change the hair color, the expert knows various coloring systems depending on the coloring requirements. Oxidation dyes are usually used for permanent, intensive dyeing's with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between about 5 and about 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user desires a particularly long-lasting coloring of his hair, the use of oxidative dyes is his only option so far. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes.

EP 2168633 B1 deals with the task of producing long-lasting hair colorations using pigments. The paper teaches that when a combination of pigment, organic silicon compound, hydrophobic polymer and a solvent is used on hair, it is possible to create colorations that are said to be particularly resistant to shampooing.

In WO 2018/115059 A1 a dyeing process is described, which runs in several steps. One step involves the application of an organ silane, and another step involves the application of a direct dye to the hair. This process is also used to achieve dyeing's with good wash fastness properties.

However, when reworking the above gauges, it has been found that the dyes obtained in this way leave the hair with a poor feel. Due to their high insolubility, the pigments used in these gauges are present in particle form in the colorant. In trials, it has been found that these particles are deposited on the surface of the hair during the coloring process, and this deposit creates a rough and dull feeling on the surface of the hair. Appropriately colored strands of hair feel shaggy, are brittle and are difficult to comb.

In addition, it has been shown that the use of the organic silicon compounds or organ silanes can also be associated with a deterioration in hair feel. As reactive compounds, the silanes produce a film on the hair fibers (or on the keratin material) via oligomerization or polymerization. Depending on the amount used and the structural nature of the organ silane, this film can be described as oily, sticky, slippery or generally weighing down the hair. All these properties the user finds very unpleasant on his hair.

BRIEF SUMMARY

The purpose of the present intention was to provide a dyeing system with fastness properties comparable to those of oxidative dyeing. Wash fastness properties should be outstanding, but the use of oxidation dye precursors normally used for this purpose should be avoided. A technology was sought that would make it possible to fix colorant compounds known from the prior art (such as pigments or direct-acting dyes) to the hair in an extremely durable manner. However, this should not negatively affect the feel and combability of the hair. After coloring, the hair should be colored with high color intensity, but still easy to comb and not feel oily.

Surprisingly, it has now been found that the task can be excellently solved if keratinous materials, in particular hair, are colored by a process in which at least three agents (a), (b) and (c) are applied to the keratinous materials (hair). Here, agent (a) contains at least one organic silicon compound, agent (b) contains at least one pigment and/or direct dye, and agent (c) contains at least one silicone oil. When the three agents (a), (b) and (c) were used in a dyeing process, keratin fibers could be dyed to a particularly high color intensity, while the feel of the hair was also very advantageous and left a well-groomed impression without weighing the hair down or making it look oily or sticky.

In an exemplary embodiment, a process for dyeing keratinous material is provided. The process includes applying an agent (a) to the keratinous material. The agent (a) includes at least one organic silicon compound. An agent (b) is applied to the keratinous material. The agent (b) includes at least one colorant compound selected from the group of pigments and/or direct dyes. An agent (c) is applied to the keratinous material. The agent (c) includes at least one silicone oil.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first object of the present disclosure is a method for coloring keratinous material, in particular human hair, comprising the following steps:
 Application of an agent (a) to the keratinous material, wherein the agent (a) comprises at least one organic silicon compound,
 Application of an agent (b) to the keratinous material, the agent (b) comprising at least one colorant compound selected from the group including pigments and/or direct dyes,
 Application of an agent (c) to the keratinous material, the agent (c) comprising at least one silicone oil.

Keratinic Material

Keratinous material includes hair, skin, nails (such as fingernails and/or toenails). Wool, furs, and feathers also fall under the definition of keratinous material. Preferably, keratinous material is understood to be human hair, human skin, and human nails, especially fingernails and toenails. Keratinous material is understood to be human hair.

Agent (a), (b) and (c)

In the process as contemplated herein, agents (a), (b) and (c) are applied to the keratinous material, in particular human hair. The three agents (a), (b) and (c) are different from each other.

In other words, a first subject of the present disclosure is a process for dyeing keratinous material, in particular human hair, comprising the following steps:
 Application of an agent (a) to the keratinous material, wherein the agent (a) comprises at least one organic silicon compound,
 Application of an agent (b) to the keratinous material, the agent (b) comprising at least one colorant compound selected from the group including pigments and/or direct dyes,
 Application of an agent (c) to the keratinous material, said agent (c) comprising at least one silicone oil, wherein the three agents (a), (b) and (c) are different from each other.

Agent (a)

Agent (a) is exemplified by its content of at least one organic silicon compound, in particular at least one organic silane. The organic silicon compounds or organic silanes contained in agent (a) is reactive compounds.

Composition (a) contains the organic silicon compound(s), in particular the organic silane(s), in a cosmetic carrier which may be hydrated, low in water or anhydrous. In addition, the cosmetic carrier can be liquid, gel-like, creamy, powdery, or even solid (e.g., in the form of a tablet or pellet). Preferably, the cosmetic carrier of the product (a) is an aqueous or aqueous-alcoholic carrier. To hair coloration, such carriers are, for example, creams, emulsions, gels, or surfactant-containing foaming solutions, such as shampoos, foam aerosols, foam formulations or other preparations suitable for application to the hair.

The cosmetic carrier preferably contains water, which means that the carrier contains at least about 2% by weight of water based on its weight. Preferably, the water content is above about 5 wt. %, further preferably above about 10 wt. %, still further preferably above about 15 wt. %. The cosmetic carrier can also be aqueous alcoholic. [0206] Aqueous/alcoholic solutions in the context of the present disclosure are aqueous solutions containing from about 2 to about 70% by weight of a $C_1$-$C_4$ alcohol, more particularly ethanol or isopropanol. The agents as contemplated herein may additionally contain other organic solvents, such as methoxy butanol, benzyl alcohol, ethyl diglycol or 1,2-propylene glycol. Preferred are all water-soluble organic solvents.

The term "dyeing agent" is used in the context of this present disclosure for a coloration of the keratin material, of the hair, caused using pigments and/or direct dyes. In this staining process, the colorant compounds are deposited in a particularly homogeneous and smooth film on the surface of the keratin material or diffuse into the keratin fiber. The film is formed in situ by oligomerization or polymerization of the organic silicon compound(s), as well as by the interaction of organic silicon compound with the colorant compounds.

Organic Silicon Compounds

As an essential ingredient of the present disclosure, the agent (a) contains at least one organic silicon compound. Preferred organic silicon compounds as contemplated herein are selected from silanes having one, two or three silicon atoms.

Organic silicon compounds, alternatively called organosilicon compounds, are compounds which either have a direct silicon-carbon bond (Si—C) or in which the carbon is bonded to the silicon atom via an oxygen, nitrogen, or sulfur atom. The organic silicon compounds of the present disclosure are preferably compounds containing one to three silicon atoms. Organic silicon compounds preferably contain one or two silicon atoms.

The agent (a) particularly preferably contains at least one organic silicon compound selected from silanes having one, two or three silicon atoms.

According to IUPAC rules, the term silane chemical compounds based on a silicon skeleton and hydrogen. In organic silanes, the hydrogen atoms are completely or partially replaced by organic groups such as (substituted) alkyl groups and/or alkoxy groups. In organic silanes, some of the hydrogen atoms may also be replaced by hydroxy groups.

In a particularly preferred embodiment, a process as contemplated herein is exemplified by the application of an agent (a) to the keratinous material, the agent (a) comprising at least one organic silicon compound selected from silanes having one, two or three silicon atoms.

The agent (a) particularly preferably comprises at least one organic silicon compound selected from silanes having one, two or three silicon atoms, the organic silicon compound further comprising one or more basic chemical functions and one or more hydroxyl groups or hydrolysable groups per molecule.

In a particularly preferred embodiment, a method as contemplated herein is exemplified by the application of an agent (a) to the keratinous material, said agent (a) comprising at least one organic silicon compound selected from silanes having one, two or three silicon atoms, said organic silicon compound further comprising one or more basic chemical functions and one or more hydroxyl groups or hydrolysable groups per molecule.

This basic group can be, for example, an amino group, an alkylamino group or a dialkylamino group, which is preferably connected to a silicon atom via a linker. The basic group is preferably an amino group, a $C_1$-$C_6$ alkylamino group or a di($C_1$-$C_6$)alkylamino group.

The hydrolysable group(s) is (are) preferably a $C_1$-$C_6$ alkoxy group, especially an ethoxy group or a methoxy group. It is preferred when the hydrolysable group is directly bonded to the silicon atom. For example, if the hydrolysable group is an ethoxy group, the organic silicon compound preferably contains a structural unit R'R"R'"Si—O—CH$_2$—CH$_3$. The residues R', R" and R'" represent the three remaining free valences of the silicon atom.

A particularly preferred method as contemplated herein the composition comprises (a) at least one organic silicon compound selected from silanes having one, two or three silicon atoms, the organic silicon compound preferably comprising one or more basic chemical functions and one or more hydroxyl groups or hydrolysable groups per molecule.

Particularly good results could be obtained if the agent as contemplated herein (a) contains at least one organic silicon compound of formula (I) and/or (II).

In another very particularly preferred embodiment, a process as contemplated herein an agent (a) is applied to the keratinous material (or human hair), the agent (a) comprising at least one organic silicon compound (a) of the formula (I) and/or (II),

where
R$_1$, R$_2$ independently represent a hydrogen atom or a $C_1$-$C_6$ alkyl group,
L is a linear or branched divalent $C_1$-$C_{20}$ alkylene group,
R3 represents a hydrogen atom or a $C_1$—C alkyl group
R4 represents a C1-C6 alkyl group
a, stands for an integer from 1 to 3, and
b stands for the integer 3−a,

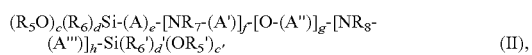

where
R5, R5', R5" independently represent a hydrogen atom or a $C_1$-$C_6$ alkyl group,
R6, R6' and R6" independently represent a $C_1$-$C_6$ alkyl group,
A, A', A", independently of one another represent a linear or branched divalent $C_1$-$C_{20}$ alkylene group
R$_7$ and R$_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III)

c, stands for an integer from 1 to 3,
d stands for the integer 3−c,
c' stands for an integer from 1 to 3,
d' stands for the integer 3−c',
c" stands for an integer from 1 to 3,
d" stands for the integer 3−c",
e stands for 0 or 1,
f stands for 0 or 1,
g stands for 0 or 1,
h stands for 0 or 1,
provided that at least one of e, f, g, and h is different from 0.

The substituents R$_1$, R$_2$, R$_3$, R$_4$, R$_5$, R$_5$', R$_5$", R$_6$, R$_6$', R$_6$", R$_7$, R$_8$, L, A', A"" and A"" in the compounds of formula (I) and (II) are explained below as examples:
Examples of a $C_1$-$C_6$ alkyl group are the groups methyl, ethyl, propyl, isopropyl, n-butyl, s-butyl, and t-butyl, n-pentyl and n-hexyl. Propyl, ethyl, and methyl are preferred alkyl radicals. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a hydroxy $C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino $C_1$-$C_6$ alkyl group are the aminomethyl group, the 2-aminoethyl group, the 3-aminopropyl group. The 2-aminoethyl group is particularly preferred. Examples of a linear divalent $C_1$-$C_{20}$ alkylene group include the methylene group (—CH$_2$—),), the ethylene group (—CH$_2$—CH$_2$—), the propylene group (—CH$_2$—CH$_2$—CH$_2$—) and the butylene group (—CH$_2$—CH$_2$—CH$_2$—). The propylene group (—CH$_2$—CH$_2$—CH$_2$—) is particularly preferred. From a chain length of 3 C atoms, divalent alkylene groups can also be branched. Examples of branched divalent $C_3$-$C_{20}$ alkylene groups are (—CH$_2$—CH(CH$_3$)—) and (—CH$_2$—CH(CH$_3$)—CH$_2$—).

In the organic silicon compounds of the formula (I)

the radicals R$_1$ and R$_2$ independently of one another represent a hydrogen atom or a $C_1$-$C_6$ alkyl group. In particular, the radicals R$_1$ and R$_2$ both represent a hydrogen atom.

In the middle part of the organic silicon compound is the structural unit or the linker -L- which stands for a linear or branched, divalent $C_1$-$C_{20}$ alkylene group.

Preferably -L- stands for a linear, divalent $C_1$-$C_{20}$ alkylene group. Further preferably -L- stands for a linear divalent $C_1$-$C_6$ alkylene group. Particularly preferred -L- stands for a methylene group (CH$_2$—), an ethylene group (—CH$_2$—CH$_2$—), propylene group (—CH$_2$—CH$_2$—CH$_2$—) or butylene (—CH$_2$—CH$_2$—CH$_2$—CH$_2$—). L stands for a propylene group (—CH$_2$—CH$_2$—CH$_2$—)

The organic silicon compounds of formula (I)

one end of each carries the silicon-containing group —Si(OR$_3$)$_a$(R$_4$)$_b$

In the terminal structural unit —Si(OR$_3$)$_a$(R$_4$)$_b$, R$_3$ is hydrogen or $C_1$-$C_6$ alkyl group, and R$_4$ is $C_1$-$C_6$ alkyl group. R3 and R$_3$ independently of each other represent a methyl group or an ethyl group.

Here a stands for an integer from 1 to 3, and b stands for the integer 3−a. If a stands for the number 3, then b is equal to 0. If a stands for the number 2, then b is equal to 1. If a stands for the number 1, then b is equal to 2.

Dyes with the best wash fastness values could be obtained if the pretreatment agent contains at least one organic silicon compound corresponding to formula (I): in which R$_3$, R$_4$ independently of one another represent a methyl group or an ethyl group.

Furthermore, dyeing's with the best wash fastness properties could be obtained if the agent as contemplated herein contains at least one organic silicon compound of formula (I) in which the radical a represents the number 3. In this case the rest b stands for the number 0.

In another preferred embodiment, an agent as contemplated herein contains (a) at least one organic silicon compound of formula (I), where
R₃, R₄ independently of one another represent a methyl group or an ethyl group and
a stands for the number 3 and
b stands for the number 0.

In another preferred embodiment, a process as contemplated herein the agent (a) contains at least one organic silicon compound of formula (I), $$R_1R_2N\text{-}L\text{-}Si(OR_3)_a(R_4)_b \qquad (I),$$

where
R₁, R₂ both represent a hydrogen atom, and
L represents a linear, divalent $C_1$-$C_6$-alkylene group, preferably a propylene group (—CH₂—CH₂—CH₂—) or an ethylene group (—CH₂—CH₂—),
R₃ represents a hydrogen atom, an ethyl group, or a methyl group,
R₄ represents a methyl group or an ethyl group,
a stands for the number 3 and
b stands for the number 0.

When b is 0, the radical R₄ does not occur in the compounds of formula (I).

Accordingly, in a further preferred embodiment, a process as contemplated herein the agent (a) comprises at least one organic silicon compound of formula (I), $$R_1R_2N\text{-}L\text{-}Si(OR_3)_a(R_4)_b \qquad (I),$$

where
R₁, R₂ both represent a hydrogen atom, and
L represents a linear, divalent $C_1$-$C_6$-alkylene group, preferably a propylene group (—CH₂—CH₂—CH₂—) or an ethylene group (—CH₂—CH₂—),
R₃ represents a hydrogen atom, an ethyl group, or a methyl group,
a stands for the number 3 and
b stands for the number 0.

Organic silicon compounds of the formula (I) which are particularly suitable for solving the problem as contemplated herein are
(3-Aminopropyl)triethoxysilan

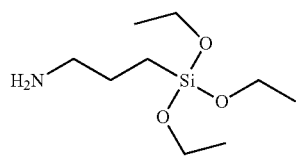

(3-Aminopropyl)trimethoxysilane

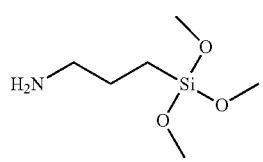

1-(3-Aminopropyl)silantriol

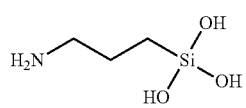

(2-Aminoethyl)triethoxysilan

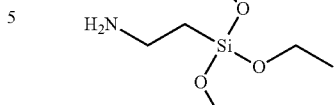

(2-Aminoethyl)trimethoxysilane

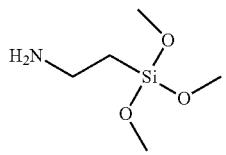

1-(2-Aminoethyl)silantriol

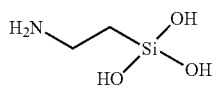

(3-Dimethylaminopropyl)triethoxysilan

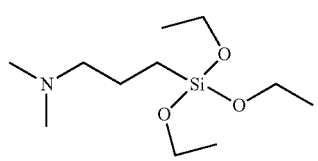 [SMILES: CCO[Si](CCCN(C)C)(OCC)OCC]

(3-Dimethylaminopropyl)trimethoxysilane

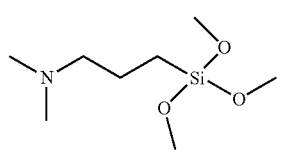

1-(3-Dimethylaminopropyl)silantriol

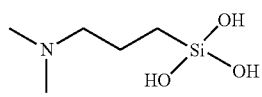

(2-Dimethylaminoethyl)triethoxysilan.

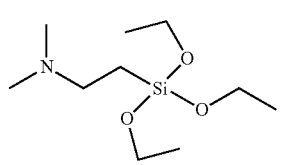

(2-Dimethylaminoethyl)trimethoxysilane and/or

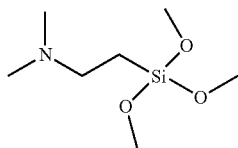

1-(2-Dimethylaminoethyl)silantriol

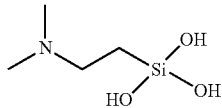

In a further preferred embodiment, a process as contemplated herein the agent (a) comprises at least one organic silicon compound of formula (I) selected from the group including
(3-Aminopropyl)triethoxysilan
(3-Aminopropyl)trimethoxysilane
1-(3-Aminopropyl)silantriol
(2-Aminoethyl)triethoxysilan
(2-Aminoethyl)trimethoxysilane
1-(2-Aminoethyl)silantriol
(3-Dimethylaminopropyl)triethoxysilan
(3-Dimethylaminopropyl)trimethoxysilane
1-(3-Dimethylaminopropyl)silantriol
(2-Dimethylaminoethyl)triethoxysilan.
(2-Dimethylaminoethyl)trimethoxysilane and/or
1-(2-Dimethylaminoethyl)silantriol.

The organic silicon compound of formula (I) is commercially available. (3-aminopropyl)trimethoxysilane, for example, can be purchased from Sigma-Aldrich. Also (3-aminopropyl)triethoxysilane is commercially available from Sigma-Aldrich.

In a further version, the present disclosure contains at least one organic silicon compound of formula (II)

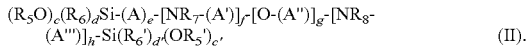

The organosilicon compounds of formula (II) as contemplated herein each carry the silicon-containing groups $(R_5O)_c(R_6)_dSi-$ and $-Si(R_6')_{d'}(OR_5')_{c'}$ at both ends.

In the central part of the molecule of formula (II) there are the groups $-(A)_e-$ and $-[NR_7-(A')]_f-$
and $-[O-(A'')]_g-$ and $-[NR_8-(A''')]_h-$. Here, each of the radicals e, f, g, and h can independently of one another stand for the number 0 or 1, with the proviso that at least one of the radicals e, f, g, and h is different from 0. In other words, an organic silicon compound of formula (II) as contemplated herein contains at least one grouping from the group including $-(A)-$ and $-[NR_7-(A')]-$ and $-[O-(A'')]-$ and $-[NR_8-(A''')]-$.

In the two terminal structural units $(R_5O)_c(R_6)_dSii-$ and $-Si(R_6')_{d'}(OR_5')_{c'}$, the radicals R5, R5', R5" independently of one another represent a hydrogen atom or a $C_1-C_6$ alkyl group. The radicals R6, R6' and R6" independently represent a $C_1-C_6$ alkyl group.

Here a stands for an integer from 1 to 3, and d stands for the integer 3−c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3−c'. If c' stands for the number 3, then d' is 0. If c' stands for the number 2, then d' is 1. If c' stands for the number 1, then d' is 2.

Dyeing's with the best wash fastness values could be obtained if the residues c and c' both stand for the number 3. In this case d and d' both stand for the number 0.

In another preferred embodiment, a process as contemplated herein the agent (a) contains at least one organic silicon compound of formula (II),

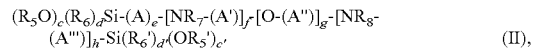

where
R5 and R5' independently represent a methyl group or an ethyl group,
c and c' both stand for the number 3 and
d and d' both stand for the number 0.

If c and c' are both the number 3 and d and d' are both the number 0, the organic silicon compound of the present disclosure corresponds to formula (IIa)

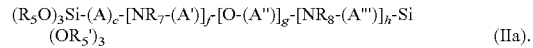

The radicals e, f, g, and h can independently stand for the number 0 or 1, whereby at least one radical from e, f, g, and h is different from zero. The abbreviations e, f, g, and h thus define which of the groupings $-(A)e-$ and $-[NR7-(A')]f-$ and $-[O-(A'')]g-$ and $-[NR8-(A''')]h-$ are in the middle part of the organic silicon compound of formula (II).

In this context, the presence of certain groupings has proved to be particularly beneficial in terms of increasing washability. Particularly good results were obtained when at least two of the residues e, f, g, and h stand for the number 1. Especially preferred e and f both stand for the number 1. Furthermore, g and h both stand for the number 0.

If e and f both stand for the number 1 and g and h both stand for the number 0, the organic silicon compound as contemplated herein corresponds to formula (IIb)

The radicals A, A', A", A''' and A"" independently represent a linear or branched divalent $C_1-C_{20}$ alkylene group. Preferably the radicals A, A', A", A''' and A"" independently of one another represent a linear, divalent $C_1-C_{20}$ alkylene group. Further preferably the radicals A, A', A", A''' and A"" independently represent a linear divalent $C_1-C_6$ alkylene group. In particular, the radicals A, A', A", A''' and A''' independently of one another represent a methylene group ($-CH_2-$), an ethylene group ($-CH_2-CH_2-$), a propylene group ($-CH_2-CH_2-CH_2-$) or a butylene group ($-CH_2-CH_2-CH_2-CH_2-$). In particular, the residues A, A', A", A''' and A"" stand for a propylene group ($-CH_2-CH_2-CH_2-$).

If the radical f represents the number 1, then the organic silicon compound of formula (II) as contemplated herein contains a structural grouping $-[NR_7-(A')]-$. If the radical f represents the number 1, then the organic silicon compound of formula (II) as contemplated herein contains a structural grouping $-[NR_8-(A''')]-$.

Wherein $R_7$ and $R_7$ independently represent a hydrogen atom, a $C_1-C_6$ alkyl group, a hydroxy-$C_1-C_6$ alkyl group, a $C_2-C_6$ alkenyl group, an amino-$C_1-C_6$ alkyl group or a group of the formula (III)

Very preferably, $R_7$ and $R_8$ independently represent a hydrogen atom, a methyl group, a 2-hydroxyethyl group, a 2-alkenyl group, a 2-aminoethyl group or a group of formula (III).

If the radical f represents the number 1 and the radical h represents the number 0, the organic silicon compound as contemplated herein contains the grouping $[NR_7\text{-}(A')]$ but not the grouping $-[NR_8\text{-}(A''')]$. If the radical R7 now stands for a grouping of the formula (III), the agent (a) contains an organic silicone compound with 3 reactive silane groups.

In another preferred embodiment, a process as contemplated herein the agent (a) contains at least one organic silicon compound of formula (II), $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II),$$

where
e and f both stand for the number 1,
g and h both stand for the number 0,
A and A' independently represent a linear, divalent $C_1$-$C_6$ alkylene group
and
R7 represents a hydrogen atom, a methyl group, a 2-hydroxyethyl group, a 2-alkenyl group, a 2-aminoethyl group or a group of formula (III).

In a further preferred embodiment, a process as contemplated herein the agent (a) comprises at least one organic silicon compound of the formula (II), wherein
e and f both stand for the number 1,
g and h both stand for the number 0,
A and A' independently of one another represent a methylene group ($-CH_2-$), an ethylene group ($-CH_2-CH_2-$) or a propylene group ($-CH_2-CH_2-CH_2-$),
and
R7 represents a hydrogen atom, a methyl group, a 2-hydroxyethyl group, a 2-alkenyl group, a 2-aminoethyl group or a group of formula (III).

Organic silicon compounds of the formula (II) which are well suited for solving the problem as contemplated herein are
3-(trimethoxysilyl)-N-[3-(trimethoxysilyl)propyl]-1-propanamine

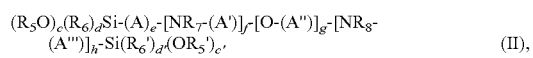

3-(Triethoxysilyl)-N-[3-(triethoxysilyl)propyl]-1-propanamine

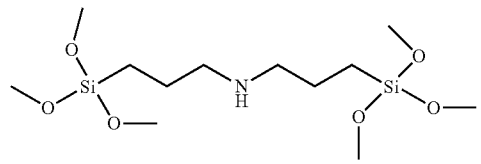

N-methyl-3-(trimethoxysilyl)-N-[3-(trimethoxysilyl)propyl]-1-propanamine

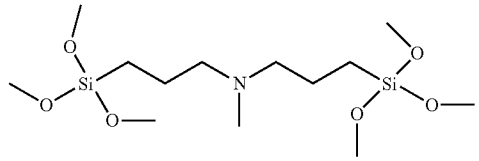

N-Methyl-3-(triethoxysilyl)-N-[3-(triethoxysilyl)propyl]-1-propanamine

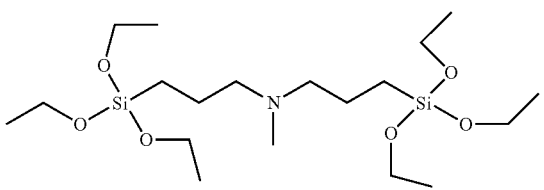 [SMILES: CCO[Si](CCCN(C)CCC[Si](OCC)(OCC)OCC)(OCC)OCC]

2-[Bis[3-(trimethoxysilyl)propyl]amino]-ethanol

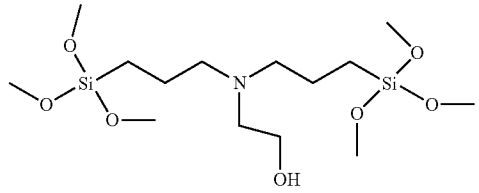

2-[bis[3-(triethoxysilyl)propyl]amino]ethanol

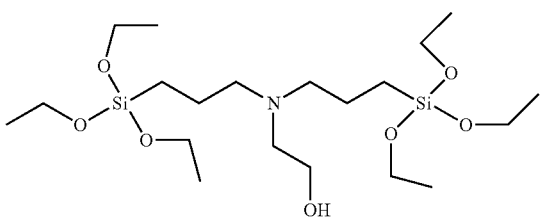 [SMILES: CCO[Si](CCCN(CCO)CCC[Si](OCC)(OCC)OCC)(OCC)OCC]

3-(Trimethoxysilyl)-N,N-bis[3-(trimethoxysilyl)propyl]-1-propanamine

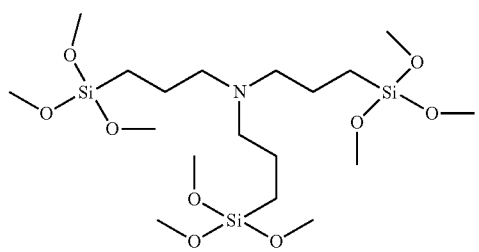

3-(Triethoxysilyl)-N,N-bis[3-(triethoxysilyl)propyl]-1-propanamine

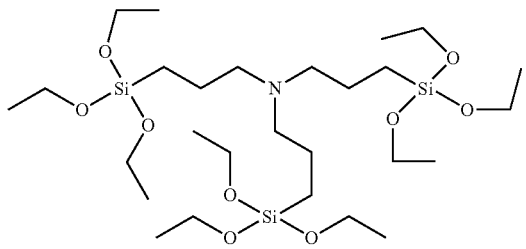 [SMILES: CCO[Si](CCCN(CCC[Si](OCC)(OCC)OCC)CCC[Si](OCC)(OCC)OCC)(OCC)OCC]

N1,N1-Bis[3-(trimethoxysilyl)propyl]-1,2-ethanediamine,

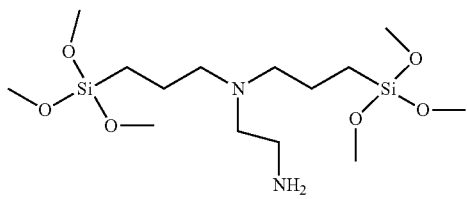

N1,N1-Bis[3-(triethoxysilyl)propyl]-1,2-ethanediamine,

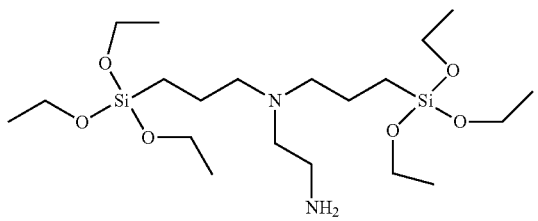 [SMILES: CCO[Si](CCCN(CCN)CCC[Si](OCC)(OCC)OCC)(OCC)OCC]

N,N-Bis[3-(trimethoxysilyl)propyl]-2-propen-1-amine

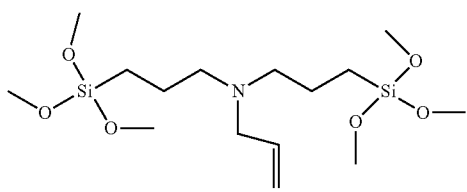

N,N-Bis[3-(triethoxysilyl)propyl]-2-propen-1-amine

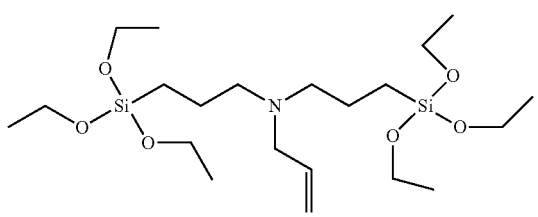 [SMILES: C=CCN(CCC[Si](OCC)(OCC)OCC)CCC[Si](OCC)(OCC)OCC]

The organic silicon compounds of formula (II) are commercially available.
Bis(trimethoxysilylpropyl)amines with the CAS number 82985-35-1 can be purchased from Sigma-Aldrich.
Bis[3-(triethoxysilyl)propyl]amines with the CAS number 13497-18-2 can be purchased from Sigma-Aldrich, for example.
N-methyl-3-(trimethoxysilyl)-N-[3-(trimethoxysilyl)propyl]-1-propanamine is alternatively referred to as bis(3-trimethoxysilylpropyl)-N-methylamine and can be purchased commercially from Sigma-Aldrich or Fluorochem.
3-(triethoxysilyl)-N,N-bis[3-(triethoxysilyl)propyl]-1-propanamine with the CAS number 18784-74-2 can be purchased for example from Fluorochem or Sigma-Aldrich.

In another preferred embodiment, an agent as contemplated herein contains (a) at least one organic silicon compound of formula (II) selected from the group including
3-(trimethoxysilyl)-N-[3-(trimethoxysilyl)propyl]-1-propanamine
3-(Triethoxysilyl)-N-[3-(triethoxysilyl)propyl]-1-propanamine
N-methyl-3-(trimethoxysilyl)-N-[3-(trimethoxysilyl)propyl]-1-propanamine
N-Methyl-3-(triethoxysilyl)-N-[3-(triethoxysilyl)propyl]-1-propanamine
2-[Bis[3-(trimethoxysilyl)propyl]amino]-ethanol
2-[bis[3-(triethoxysilyl)propyl]amino]ethanol
3-(Trimethoxysilyl)-N,N-bis[3-(trimethoxysilyl)propyl]-1-propanamine
3-(Triethoxysilyl)-N,N-bis[3-(triethoxysilyl)propyl]-1-propanamine
N1,N1-bis[3-(trimethoxysilyl)propyl]-1,2-ethanediamine,
N1,N1-bis[3-(triethoxysilyl)propyl]-1,2-ethanediamine,
N,N-bis[3-(trimethoxysilyl)propyl]-2-propen-1-amine and/or
N,N-bis[3-(triethoxysilyl)propyl]-2-propen-1-amine.

In further dyeing tests, it has also proved to be particularly advantageous if the agent used on the keratinous material in the process as contemplated herein (a) contains at least one organic silicon compound of formula (IV)

$$R_9Si(OR_{10})_k(R_{11})_m \qquad (IV).$$

The organic silicon compound(s) of formula (IV) may also be called a silane of the alkyl-alkoxy-silane or alkyl-hydroxy-silane type, $$R_9Si(OR_{10})_k(R_{11})_m \qquad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3−k.

In another preferred embodiment, a process as contemplated herein the agent (a) contains at least one organic silicon compound of formula (IV).

$$R_9Si(OR_{10})_k(R_{11})_m \qquad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3−k.

In a further preferred embodiment, a process as contemplated herein the agent (a) contains, in addition to the organic silicon compound(s) of formula (I), at least one further organic silicon compound of formula (IV)

$$R_9Si(OR_{10})_k(R_{11})_m \qquad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3−k.

In a further preferred embodiment, a process as contemplated herein the agent (a) contains, in addition to the organic silicon compound or compounds of the formula (II), at least one further organic silicon compound of the formula (IV)

$$R_9Si(OR_{10})_k(R_{11})_m \quad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3−k.

In a further preferred embodiment, a process as contemplated herein the composition contains (a) in addition to the organic silicon compound(s) of formula (I) and/or (II) at least one further organic silicon compound of formula (IV)

$$R_9Si(OR_{10})_k(R_{11})_m \quad (IV),$$

where
$R_9$ represents a $C_1$-$C_{12}$ alkyl group,
$R_{10}$ represents a hydrogen atom or a $C_1$-$C_6$ alkyl group,
$R_{11}$ represents a $C_1$-$C_6$ alkyl group
k is an integer from 1 to 3, and
m stands for the integer 3−k.

In the organic silicon compounds of formula (IV), the radical $R_9$ represents a $C_1$-$C_{12}$ alkyl group. This $C_1$-$C_{12}$ alkyl group is saturated and can be linear or branched. Preferably R9 stands for a linear $C_1$-$C_{12}$ alkyl group. Preferably $R_9$ stands for a methyl group, an ethyl group, an n-propyl group, an n-butyl group, an n-pentyl group, an n-hexyl group, an n-octyl group or an n-dodecyl group. Particularly preferred, R9 stands for a methyl group, an ethyl group or an n-octyl group.

In the organic silicon compounds of formula (IV), the radical $R_{10}$ represents a hydrogen atom or a $C_1$-$C_6$ alkyl group. R10 stands for a methyl group or an ethyl group.

In the organic silicon compounds of formula (IV), the radical $R_{11}$ represents a $C_1$-$C_6$ alkyl group. R11 stands for a methyl group or an ethyl group.

Furthermore, k stands for a whole number from 1 to 3, and m stands for the whole number 3-k. If k stands for the number 3, then m is equal to 0. If k stands for the number 2, then m is equal to 1. If k stands for the number 1, then m is equal to 2.

Dyes with the best wash fastness values could be obtained if an agent (a) were used in the process which contains at least one organic silicon compound of the formula (IV) in which the radical k stands for the number 3. In this case the rest m stands for the number 0.

Organic silicon compounds of the formula (IV) which are particularly suitable for solving the problem as contemplated herein are
Methyltrimethoxysilane

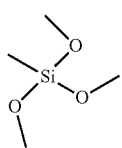

Methyltriethoxysilane

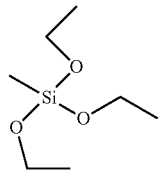

Ethyltrimethoxysilane

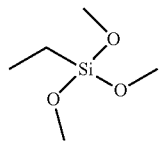

Ethyltriethoxysilane

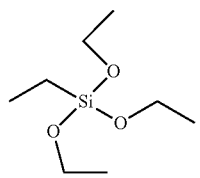

n-Hexyltrimethoxysilane

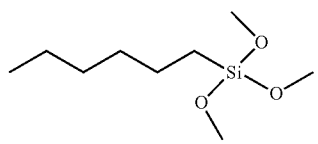

n-Hexyltriethoxysilane

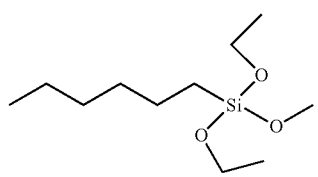

n-Octyltrimethoxysilane

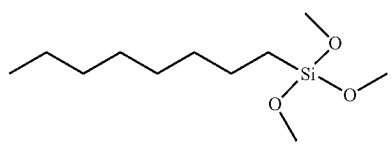

n-Octyltriethoxysilane

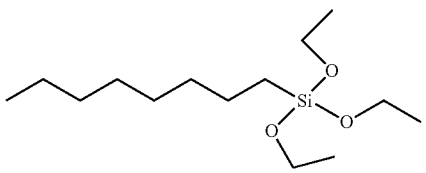 [SMILES: CCCCCCCC[Si](OCC)(OCC)OCC]

n-dodecyltrimethoxysilane and/or

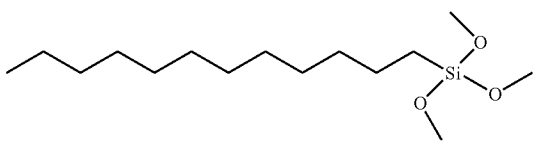 [SMILES: CCCCCCCCCCCC[Si](OC)(OC)OC]

n-dodecyltriethoxysilane.

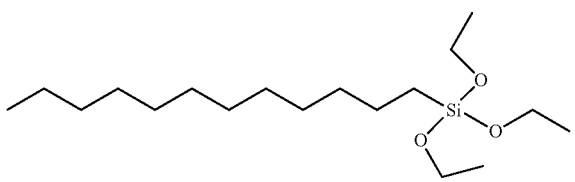 [SMILES: CCCCCCCCCCCC[Si](OCC)(OCC)OCC]

In another preferred embodiment, a process as contemplated herein the agent (a) contains at least one organic silicon compound of formula (IV) selected from the group including
Methyltrimethoxysilane
Methyltriethoxysilane
Ethyltrimethoxysilane
Ethyltriethoxysilane
Hexyltrimethoxysilane
Hexyltriethoxysilane
Octyltrimethoxysilane
Octyltriethoxysilane
Dodecyltrimethoxysilane and/or
Dodecyltriethoxysilane.

In an explicitly particularly preferred embodiment, a process as contemplated herein an agent (a) is applied to the keratinous material which contains at least one organic silicon compound of the formula (I) which is selected from the group including
(3-aminopropyl)triethoxysilane and (3-aminopropyl) trimethoxysilane, and additionally contains at least one organic silicone compound of formula (IV) selected from the group including methyltrimethoxysilane, methyltriethoxysilane, ethyltrimethoxysilane and ethyltriethoxysilane.

The organic silicon compounds described above are reactive compounds. In this context, it has been found preferable if the agent (a) as contemplated herein contains—based on the total weight of the agent (a)—one or more organic silicon compounds in a total amount of from about 0.1 to about 20.0% by weight, preferably from about 0.5 to about 15.0% by weight and particularly preferably from about 5.0 to about 10.0% by weight.

In this context, it has been found to be particularly preferred if the agent (a) as contemplated herein contains—based on the total weight of the agent (a)—one or more organic silicon compounds of the formula (I) and/or (II) in a total amount of from about 0.1 to about 20.0% by weight, preferably from about 0.2 to about 15.0% by weight and particularly preferably from about 0.2 to about 3.0% by weight.

It has further been found to be particularly preferred if the agent (a) as contemplated herein contains—based on the total weight of the agent (a)—one or more organic silicon compounds of the formula (IV) in a total amount of from about 0.1 to about 20.0% by weight, preferably from about 0.5 to about 15.0% by weight and particularly preferably from about 2.0 to about 8.0% by weight.

Particularly resistant strains could be obtained when using an alkaline adjusted agent (a). Preferably, agent (a) contains water and has a pH of from about 7.0 to about 11.5, preferably from about 7.5 to about 11.0, and more preferably from about 8.0 to about 10.5.

In another very particularly preferred embodiment, a process as contemplated herein the agent (a) has a pH of from about 7.0 to about 11.5, preferably from about 7.5 to about 11.0 and particularly preferably from about 8.0 to about 10.5.

Agent (b)

The agent (b) is exemplified by its content of at least one pigment and/or a direct dye. The agent (b) may also be called colorant (b).

Pigments within the meaning of the present disclosure are coloring compounds which have a solubility in water at about 25° C. of less than about 0.5 g/L, preferably less than about 0.1 g/L, even more preferably less than about 0.05 g/L. Water solubility can be determined, for example, by the method described below: about 0.5 g of the pigment are weighed in a beaker. A stir-fish is added. Then one liter of distilled water is added. This mixture is heated to about 25° C. for one hour while stirring on a magnetic stirrer. If undissolved components of the pigment are still visible in the mixture after this period, the solubility of the pigment is below about 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below about 0.5 g/L.

Suitable color pigments can be of inorganic and/or organic origin.

In a preferred embodiment, an agent (b) of the present disclosure contains at least one colorant compound from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferro-cyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, a process as contemplated herein the agent (b) contains at least one colorant compound from the group of pigments selected from the group of colored metal oxides, metal hydroxides, metal oxide hydrates, silicates, metal sulfides, complex metal cyanides, metal sulfates, bronze pigments and/or from colored pigments based on mica or mica which are coated with at least one metal oxide and/or one metal oxychloride.

In a further preferred embodiment, an agent as contemplated herein contains (b) at least one colorant compound from the group of pigments selected from pigments based on mica or micaceous iron oxide, which is combined with one or more metal oxides from the group of titanium dioxide (CI 77891), are coated with black iron oxide (CI 77499), yellow iron oxide (CI 77492), red and/or brown iron oxide (CI 77491, CI 77499), manganese violet (CI 77742), ultramarine (sodium aluminum sulfo silicates, CI 77007, pigment blue 29), chromium oxide hydrate (CI 77289), chromium oxide (CI 77288) and/or iron blue (ferric ferrocyanides, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:
Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491(Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)

Other particularly preferred color pigments with the trade name Xirona® are for example:
Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.

In addition, particularly preferred color pigments with the trade name Unipure® are for example:
Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica In a further embodiment, the means as contemplated herein may also contain (b) one or more coloring compounds from the group of organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyrrole, indigo, thioindido, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In a further particularly preferred embodiment, a process as contemplated herein the agent (b) contains at least one colorant compound from the group of organic pigments selected from the group of carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above-mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the pigments in agent (b) of the process as contemplated herein is particularly preferred. It is also preferred if the pigments used have a certain particle size. As contemplated herein, it is advantageous if the at least one pigment has a mean particle size D50 of from about 1.0 to about 50 µm, preferably from about 5.0 to about 45 µm, preferably from about 10 to about 40 µm, from about 14 to about 30 µm. The mean particle size $D50D_{50}$, for example, can be determined using dynamic light scattering (DLS).

The pigment or pigments may be used in an amount of from about 0.001 to about 20% by weight, of from about 0.05 to about 5% by weight, each based on the total weight of agent (b).

As colorant compounds, the agents (b) used in the process as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at about 25° C. of more than about 0.5 g/L and are therefore not to be regarded as pigments.

Preferably, the direct dyes within the meaning of the present disclosure have a solubility in water (760 mmHg) at about 25° C. of more than about 1.0 g/L.

Direct dyes can be divided into anionic, cationic, and non-ionic direct dyes.

In a further preferred embodiment, an agent as contemplated herein contains as coloring compound (b) at least one anionic, cationic and/or non-ionic direct dye.

In a further preferred embodiment, an agent as contemplated herein contains (b) at least one anionic, cationic and/or non-ionic direct dye.

Suitable cationic direct dyes include Basic Blue 7, Basic Blue 26, Basic Violet 2, and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

In a further preferred embodiment, a process as contemplated herein the agent (b) comprises at least one direct dye selected from the group including anionic, cationic, and nonionic direct dyes.

In the course of the work leading to the present disclosure, it has been found that dyeing's of particularly high color intensity can be produced with agents (b) containing at least one anionic direct dye.

In an explicitly quite particularly preferred embodiment, an agent (b) used in the process as contemplated herein contains at least one anionic direct dye.

Anionic direct dyes are also called acid dyes. Acid dyes are direct dyes that have at least one carboxylic acid group (—COOH) and/or one sulphonic acid group (—SO₃H). Depending on the pH value, the protonated forms (—COOH, —SO₃H) of the carboxylic acid or sulphonic acid groups are in equilibrium with their deprotonated forms (—OO⁻, —SO₃— present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at about 25° C. of more than about 0.5 g/L and are therefore not to be regarded as pigments. Preferably the acid dyes within the meaning of the present disclosure have a solubility in water (760 mmHg) at about 25° C. of more than about 1.0 g/L.

The alkaline earth salts (such as calcium salts and magnesium salts) or aluminum salts of acid dyes often have a lower solubility than the corresponding alkali salts. If the solubility of these salts is below about 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

As contemplated herein, the use of an agent (b) which contains at least one anionic direct dye selected from the group including nitrophenylenediamines, nitroaminophenols, azo dyes, anthraquinone dyes, triarylmethane dyes, xanthene dyes, rhodamine dyes, oxazine dyes and/or indophenol dyes is thus preferred, the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

For example, one or more compounds from the following group can be selected as particularly well suited acid dyes: Acid Yellow 1 (D&C Yellow 7, Citronin A, Ext. D&C Yellow No. 7, Japan Yellow 403, CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C.29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C.015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Echtrot D, FD&C Red Nr. 2, Food Red 9, Naphthol Red S), Acid Red 33 (Red 33, Fuchsia Red, D&C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C.53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet n° 2, C.I. 60730, COLIPA n° C.063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The water solubility of direct dyes can be determined, for example, in the following way. about 0.1 g of the direct dye is added to a beaker. A stir-fish is added. Then add about 100 ml of water. This mixture is heated to about 25° C. on a magnetic stirrer while stirring. It is stirred for about 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If about 0.1 g of the anionic direct dye dissolves in about 100 ml water at about 25° C., the solubility of the dye is about 1.0 g/L.

Acid Yellow 1 is called 8-hydroxy-5,7-dinitro-2-naphthalenesulfonic acid disodium salt and has a solubility in water of at least about 40 g/L (25° C.).

Acid Yellow 3 is a mixture of the sodium salts of mono- and disulfonic acids of 2-(2-quinolyl)-1H-indene-1,3(2H)-dione and has a water solubility of about 20 g/L (25° C.).

Acid Yellow 9 is the disodium salt of 8-hydroxy-5,7-dinitro-2-naphthalenesulfonic acid, its solubility in water is above about 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at about 25° C.

Acid Orange 7 is the sodium salt of 4-[(2-hydroxy-1-naphthyl)azo]benzene sulphonate. Its water solubility is more than about 7 g/L (25° C.).

Acid Red 18 is the trinatirum salt of 7-hydroxy-8-[(E)-(4-sulfonato-1-naphthyl)-diazenyl)]-1,3-naphthalene disulfonate and has a very high-water solubility of more than about 20% by weight.

Acid Red 33 is the diantrium salt of 5-amino-4-hydroxy-3-(phenylazo)-naphthalene-2,7-disulphonate, its solubility in water is about 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than about 10 g/L (25° C.).

Acid Blue 9 is the disodium salt of 2-({4-[N-ethyl(3-sulfonatobenzyl)amino]phenyl}{4-[(N-ethyl(3-sulfonatobenzyl)imino]-2,5-cyclohexadien-1-ylidene}methyl)-benzenesulfonate and has a solubility in water of more than about 20% by weight (25° C.).

A very particularly preferred process as contemplated herein the agent (b) comprises at least one anionic direct dye selected from the group including Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dye(s), in the anionic direct dyes, can be used in different amounts in the agent (b) depending on the desired color intensity. Particularly good results were obtained when the agent (b)—based on the total weight of the agent (b)—contains one or more direct dyes in a total amount of from about 0.01 to about 10.0% by weight, preferably from about 0.1 to about 8.0% by weight, more preferably from about 0.2 to about 6.0% by weight and most preferably from about 0.5 to about 4.5% by weight.

In a further preferred embodiment, an agent (b) contains—based on the total weight of the agent (b)—one or more direct dyes in a total amount of from about 0.01 to about 10.0% by weight, preferably from about 0.1 to about 8.0% by weight, more preferably from about 0.2 to about 6.0% by weight and most preferably from about 0.5 to about 4.5% by weight.

In a further preferred embodiment, an agent as contemplated herein contains—based on the total weight of the agent (b)—one or more anionic direct dyes (b) in a total amount of from about 0.01 to about 10.0% by weight, preferably from about 0.1 to about 8.0% by weight, more preferably from about 0.2 to about 6.0% by weight and very particularly preferably from about 0.5 to about 4.5% by weight.

Agent (c)

The agent (c) may be referred to as an after-treatment agent. The agent (c) is exemplified by its content of at least one silicone oil.

For the purposes of the present disclosure, the term "oil" is understood to mean a substance which is liquid at room temperature (25° C.). Furthermore, an oil as contemplated herein has a solubility in water of less than about 1 g/l, preferably less than about 0.5 g/l, more preferably less than about 0.1 g/l (measured at 25° C.).

The water solubility of the silicone oil can be determined, for example, in the following way: about 1.0 g of the silicone oil is added to a beaker. Then about 1000 ml (1 liter) of water is added. A stir-fish is added, and the mixture is heated to about 25° C. on a magnetic stirrer while stirring. It is stirred for about 60 minutes. The aqueous mixture is then visually assessed. If a second phase is still visible after this period, i.e., a separately present oil phase in addition to the water phase, then the solubility of the silicone oil is less than about 1 g/l (1 gram/liter).

The silicone oils contained in agent (c) are polymeric compounds whose molecular weight is at least about 500 g/mol, preferably at least about 1000 g/mol, further preferably at least about 2500 g/mol, and particularly preferably of at least about 5000 g/mol.

The silicone oils contained in agent (c) comprise Si—O repeating units, where the Si atoms may carry organic radicals such as alkyl groups or substituted alkyl groups.

Corresponding to the high molecular weight of silicone oils, these are based on more than about 10 Si—O repeating units, preferably more than about 50 Si—O repeating units and particularly preferably more than about 100 Si—O repeating units.

The silicone oils contained in agent (c) are therefore different from the organic silicon compounds of agent (a).

In other words, a first object of the present disclosure is a method for coloring keratinous material, in particular human hair, comprising the following steps:

Application of an agent (a) to the keratinous material, wherein the agent (a) contains at least one organic silicon compound having one, two or three silicon atoms, Application of an agent (b) to the keratinous material, the agent (b) comprising at least one colorant compound selected from the group including pigments and/or direct dyes, Application of an agent (c) to the keratinous material, wherein the agent (c) comprises at least one polymeric silicone oil.

In other words, a first object of the present disclosure is a method for coloring keratinous material, in particular human hair, comprising the following steps:

Application of an agent (a) to the keratinous material, wherein the agent (a) contains at least one organic silicon compound having one, two or three silicon atoms, Application of an agent (b) to the keratinous material, the agent (b) comprising at least one colorant compound selected from the group including pigments and/or direct dyes, Application of an agent (c) to the keratinous material, the agent (c) containing at least one silicone oil comprising more than about 10 silicon atoms, preferably more than about 50 silicon atoms, particularly preferably more than about 100 silicon atoms.

In the course of the work leading to the present disclosure, it was found that the viscosity of the silicone oil used in agent (c) can have a strong influence on the feel and condition of the colored keratin material (or hair).

In the process as contemplated herein, the application of agent (a) first generates a film of organosilicon compounds (i.e., silanes) on the keratin material, which has an extremely high affinity for the keratins. In interaction with the colorant compounds of agent (b), a layer of colorant compounds is now formed on the keratin, the colorant compounds being fixed on the keratin by the silane layer. It has been found that the formation of these layers or films on the hair without further post-treatment can leave a very unpleasant feeling on the keratin material that must be described as occupied, "oily" and in extreme cases even "slippery".

By applying another agent (c), this hair feeling could now be extremely improved. Keratin fibers (hairs) that left a very occupied, oily impression without post-treatment (i.e., only with application of agents (a) and (b)) were perceived as drier, less oily, and less occupied in their feel by application of post-treatment agent (c).

If the keratin materials were additionally treated with an agent (c) containing (polymeric) silicone oils, it was consequently possible to avoid the coated, oily feel and to produce a well-groomed appearance.

Silicone oils with a viscosity of from about 5 to about 3000 mm2/s (measured according to ASTM standard D-445) have proved to be particularly suitable for solving this problem (measured at 25° C.).

It has been found to be particularly preferred to use silicone oils with a viscosity of from about 5 to about 3000 mm2/s, preferably from about 10 to about 2000 mm2/s, more preferably from about 10 to about 1000 mm2/s, still more preferably from about 10 to about 500 mm2/s and most preferably from about 10 to about 500 mm2/s (always measured according to ASTM Standard D-445, 25° C.) in the medium (c).

In the context of a further explicitly quite particularly preferred embodiment, a process as contemplated herein the agent (c) comprises at least one silicone oil having a viscosity of from about 5 to about 3000 mm2/s, preferably from about 10 to about 2000 mm2/s, more preferably from about 10 to about 1000 mm2/s, and particularly preferably from about 10 to about 500 mm2/s, measured according to ASTM Standard D-445.

The ASTM Standard D-445 is the standard method for measuring the kinematic viscosity of transparent and opaque liquids.

Viscosity was measured according to ASTM Standard D-446, Version 06 (D445-06), published June 2006. This measurement method measures the time required for the defined volume of a liquid to flow through the kappilars of a calibrated viscometer under defined conditions. For details of the procedure, please refer to ASMT-D445, ASTM D445-06. Measurement temperature is about 25° C. Suitable equipment (such as viscometers and thermometers and the corresponding calibrations) are given in the method.

In the context of a further explicitly quite particularly preferred embodiment, a process as contemplated herein the agent (c) comprises at least one silicone oil having a viscosity of from about 5 to about 3000 mm2/s, preferably from about 10 to about 2000 mm2/s, more preferably from about 10 to about 1000 mm2/s, and particularly preferably from about 10 to about 500 mm2/s, measured according to ASTM Standard D-445 (25° C.).

In principle, various silicone oils can be used in agent (c), but the use of polydimethylsiloxanes has proved to be particularly advantageous in terms of improving the feel and reducing the oily feel of the hair.

For this reason, it is particularly preferred if the agent (c) contains at least one silicone oil from the group of polydimethylsiloxanes (dimethicones).

In the context of a further explicitly quite particularly preferred embodiment, a process as contemplated herein the agent (c) comprises at least one silicone oil from the group of polydimethylsiloxanes.

In the context of a further explicitly quite particularly preferred embodiment, a process as contemplated herein the agent (c) comprises at least one silicone oil from the group of linear polydimethylsiloxanes.

Silicone oils from the group of linear polydimethylsiloxanes are compounds of the general structure (V)

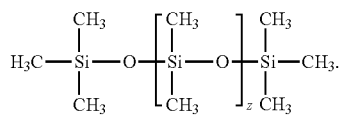

(V)

Here, z is selected so that the dimethicones are liquid and preferably have the very particularly suitable viscosity ranges.

Preferably, z can stand for an integer from about 50 to about 100000, more preferably from about 100 to about 50000, most preferably from about 500 to about 50000.

Corresponding dimethicones can be purchased commercially from various manufacturers. Particularly suitable, for example, is the dimethicone available for sale under the trade name Xiameter PMX 200 Silicone Fluid 50 CS from Dow Chemicals, which has a viscosity of about 50 mm2/s (at 25° C.). This dimethicone is the most preferred.

Another particularly well-suited dimethicone is Xiameter PMX 200 Silicone Fluid 100 CS, also available from Dow Corning, which has a viscosity of 100 mm2/s (measured at 25° C.).

Another dimethicone that is particularly well-suited to this application is the Xiameter PMX 200 Silicone Fluid 350 CS, whose viscosity is about 350 mm2/s (at 25° C.).

Another particularly well-suited dimethicone is Dow Corning 200 fluid 500 cSt, available from Dow Corning, which has a viscosity of about 500 mm2/s (at 25° C.).

The silicone oil(s) are preferentially present in the agent (c) in certain ranges of amounts. Very preferably, agent (c) contains—based on the total weight of agent (c)—one or more silicone oils in a total amount of from about 0.1 to about 25.0% by weight, preferably from about 0.5 to about 10.0% by weight, further preferably from about 1.0 to about 8.0% by weight and most preferably from about 2.0 to about 4.0% by weight.

In the context of a further preferred embodiment, a process as contemplated herein the agent (c) contains—based on the total weight of the agent (c)—one or more silicone oils in a total amount of from about 0.1 to about 25.0% by weight, preferably from about 0.5 to about 10.0% by weight, more preferably from about 1.0 to about 8.0% by weight and very particularly preferably from about 2.0 to about 4.0% by weight.

Other Ingredients in Agents (a), (b) and (c)

The previously described agents (a), (b) and (c) may further include one or more optional ingredients.

The products may also contain one or more surfactants. The term surfactants refer to surface-active substances. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —COO$^{(-)}$— or —SO$_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —SO$_3$H group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino propionates, aminoglycinate, imidazoliniumbetaines and sulfobetaines.

Particularly preferred ampholytic surfactants are N-cocoalkylaminopropionate, cocoacylaminoethylaminopropionate and $C_{12}$-$C_{18}$ acylsarcosine.

The products may also additionally contain at least one non-ionic surfactant. Suitable non-ionic surfactants are alkyl polyglycosides as well as alkylene oxide addition products to fatty alcohols and fatty acids with 2 to 30 mol ethylene oxide per mol fatty alcohol or fatty acid. Preparations with good properties are also obtained if they contain as non-ionic surfactants fatty acid esters of ethoxylated glycerol reacted with at least 2 mol ethylene oxide. The non-ionic surfactants are used in a total quantity of from about 0.1 to about 45% by weight, preferably from about 1 to about 30% by weight and very preferably from about 1 to about 15% by weight—based on the total weight of the respective agent.

In addition, the products may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually including a hydrocarbon backbone (e.g., including one or two linear or branched alkyl chains) and the positive charge(s) being in the hydrophilic head group. Examples of cationic surfactants are quaternary ammonium compounds which, as hydrophobic radicals, may carry one or two alkyl chains with a chain length of 8 to 28 C atoms, quaternary phosphonium salts substituted with one or more alkyl chains with a chain length of 8 to 28 C atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of from about 0.1 to about 45 wt. %, preferably from about 1 to about 30 wt. % and most preferably from about 1 to about 15 wt. %—based on the total weight of the respective agent.

Furthermore, the means as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

The anionic surfactants are used in a total quantity of from about 0.1 to about 45 wt. %, preferably from about 1 to about 30 wt. % and most preferably from about 1 to about 15 wt. %—based on the total weight of the respective agent.

To adjust the desired pH, agents (a), (b) and (c) may also contain at least one alkalizing agent and/or acidifying agent. The pH values for the purposes of the present disclosure are pH values measured at a temperature of about 22° C.

As alkalizing agents, agents (a), (b) and (c) may contain for example ammonia, alkanolamines and/or basic amino acids.

The alkanolamines which can be used in the composition of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment the agent as contemplated herein contains an alkanolamine selected from 2-aminoethan-1-ol and/or 2-amino-2-methylpropan-1-ol as alkalizing agent.

A particularly preferred embodiment the agent as contemplated herein contains an alkanolamine selected from 2-aminoethan-1-ol and/or 2-amino-2-methylpropan-1-ol as alkalizing agent. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than about 7.0.

Basic α-amino carboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In another particularly preferred embodiment, an agent as contemplated herein the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Acidifiers commonly used by experts are, for example, indulgence acids such as citric acid, acetic acid, malic acid, or tartaric acid, as well as diluted mineral acids such as hydrochloric acid, sulfuric acid, or phosphoric acid.

They may also contain other active substances, auxiliaries and additives, such as solvents, fatty components such as C8-C30 fatty alcohols, $C_8$-$C_{30}$ fatty acid triglycerides, $C_8$-$C_{30}$ fatty acid monoglycerides, $C_8$-$C_{30}$ fatty acid diglycerides and/or hydrocarbons; polymers, structural agents such as glucose, maleic acid and lactic acid; hair conditioning compounds such as phospholipids, for example lecithin and cephalins; perfume oils, dimethylisosorbide and cyclodextrins; fiber structure-improving active substances, in particular mono-, di- and oligosaccharides such as glucose, galactose, fructose, fructose and lactose; dyes for coloring the composition; anti-dandruff active substances such as Piroctone Olamine, Zinc Omadine and Climbazol; amino acids and oligopeptides; protein hydrolysates on animal and/or vegetable basis, as well as in the form of their fatty acid condensation products or optionally anionic or cationically modified derivatives; vegetable oils; sunscreens and UV-blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycumarine, hydroxybenzoic acids, catechine, tannine, leukoanthocyanidine, anthocyanidine, flavanone, flavone and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; and blowing agents such as propane-butane mixtures, $N_2O$, dimethyl ether, $CO_2$ and air.

Very particularly preferably, the composition (b) additionally comprises at least one anionic polymer selected from the group including the copolymers of acrylic acid, the copolymers of methacrylic acid, the homopolymers or copolymers of acrylic acid esters, the homopolymers or copolymers of methacrylic acid esters, the homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Very preferably, agent (c) additionally contains at least one cationic surfactant.

The selection of these other substances will be made by the specialist according to the desired properties of the agents. About other optional components and the quantities of these components used, explicit reference is made to the relevant manuals known to the specialist. The additional active ingredients and auxiliary substances are preferably used in the preparations as contemplated herein in quantities of from about 0.0001 to about 25 wt. % each, from about 0.0005 to about 15 wt. %, based on the total weight of the respective agent.

Process for Dyeing Keratin Materials

In the process as contemplated herein, agents (a), (b) and (c) are applied to the keratinous materials, to human hair. Thus, the agent (a), (b), and (c) are the ready-to-use means. The agent (a), (b) and (c) are different from each other.

The agent (a), (b) and (c) can in principle be applied simultaneously or successively, with successive application being preferred.

The best results were obtained when agent (a) was applied to the keratin materials as a pretreatment agent, then agent (b) was applied as a coloring agent, and subsequently agent (c) was applied as a posttreatment agent.

Therefore, a method for dyeing keratinous material, in particular human hair, comprising the following steps in the order given is particularly preferred:
in a first step, applying an agent (a) to the keratinous material, the agent (a) comprising at
least one organic silicon compound,
in a second step, applying an agent (b) to the keratinous material, the agent (b) comprising at
least one colorant compound selected from the group including pigments and/or direct dyes,
in a third step, applying an agent (c) to the keratinous material, the agent (c) comprising at least one silicone oil.

In addition, to prevent the user from perceiving an unpleasant feel of the dyed keratin material over a longer period, agents (a), (b) and (c) are particularly preferably applied within one and the same dyeing process, which means that there is a period of a maximum of several hours between the application of agents (a) and (c).

In a further preferred embodiment, a method as contemplated herein first the agent (a) is applied, then the agent (b) is applied and subsequently the agent (c) is applied, the period between the application of the agents (a) and (c) being at most about 24 hours, preferably at most about 12 hours and particularly preferably at most about 6 hours.

Within the scope of the procedure as contemplated herein, the keratin materials, in particular human hair, are first treated with agent (a). Then the actual colorant (b)—which contains the coloring compounds—is applied to the keratin materials.

Preferably, agent (a) itself does not contain colorants or coloring compounds. A characteristic feature of the pretreatment agent (a) is its content of at least one reactive organic silicon compound. The reactive organic silicon compound(s) (a) functionalize the hair surface as soon as they meet it. In this way a first, still uncolored film is formed. In the second step of the process, a colorant (b) is now applied to the hair. During application of the colorant (b), the colorant compounds interact with the silane film and are thus bound to the keratin materials. However, without application of the aftertreatment agent (c), the film formed on the hair at this stage of the procedure still left an oily or, at worst, slippery hair feels. This disadvantageous haptic can now be reduced or compensated for by the application of the agent (c) as contemplated herein. Here, the technical application properties of the resulting dyeing can be further improved by selecting the optimum process conditions.

In the context of a further form of execution, a procedure comprising the following steps in the order indicated is particularly preferred
(1) Application of agent (a) on the keratinous material,
(2) Allow the agent (a) to act for a period of from about 10 seconds to about 10 minutes, preferably from about 10 seconds to about 5 minutes,
(3) if necessary, rinse the keratinous material with water,
(4) Application of agent (b) on the keratinous material,
(5) Allow the agent (b) to act for a period of from about 30 seconds to about 30 minutes, preferably from about 30 seconds to about 10 minutes, and
(6) Rinse the keratinous material with water,
(7) Application of agent (c) on the keratinous material,
(8) allowing the agent (c) to act for a period of from about 30 seconds to about 10 minutes, preferably from about 30 seconds to about 50 minutes; and
(9) Rinse the keratinous material with water.

By rinsing the keratinous material with water in steps (3), (6) and (9) of the process, it is understood as contemplated herein that only water is used for the rinsing process, without the use of other agents different from agents (a), (b) and (c).

In a first step (1), agent (a) is applied to the keratin materials, especially human hair.

After application, the agent (a) can act on the keratin materials. In this context, application times from about 10 seconds to about 10 minutes, preferably from about 20 seconds to about 5 minutes and especially preferably from about 30 seconds to about 2 minutes on the hair have proven to be particularly beneficial.

In a preferred embodiment of the method as contemplated herein, the agent (a) can now be rinsed from the keratin materials before the agent (b) is applied to the hair in the subsequent step.

Dyeing's with also good wash fastness were obtained when agent (b) was applied to the keratin materials which were still exposed to agent (a).

In step (4), agent (b) is now applied to the keratin materials. After application, let the agent (b) act on the hair.

The process as contemplated herein allows the production of dyeing's with particularly good intensity and wash fastness even with a short exposure time of agent (b). Application times from about 10 seconds to about 10 minutes, preferably from about 20 seconds to about 5 minutes and most preferably from about 30 seconds to about 3 minutes on the hair have proven to be particularly beneficial.

In step (6), agent (b) (and any remaining agent (a)) is rinsed out of the keratin material with water.

Subsequently, the agent (c) is applied to the keratin materials in a post-treatment step. The agent (c) is also left to act on the keratin materials and then rinsed out again with water.

The positive effects achieved by agent (c) are particularly long-lasting if agent (c) is applied repeatedly—for example during regular hair washing.

In the context of a further form of execution, a procedure comprising the following steps in the order indicated is particularly preferred
(1) Application of agent (a) on the keratinous material,
(2) Allow the agent (a) to act for a period of from about 10 seconds to about 10 minutes, preferably from about 10 seconds to about 5 minutes,
(3) if necessary, rinse the keratinous material with water,
(4) Application of agent (b) on the keratinous material,
(5) Allow the agent (b) to act for a period of from about 30 seconds to about 30 minutes, preferably from about 30 seconds to about 10 minutes, and
(6) Rinse the keratinous material with water,
(7) Application of agent (c) on the keratinous material,
(8) allowing the agent (c) to act for a period of from about 30 seconds to about 10 minutes, preferably from about 30 seconds to about 50 minutes; and
(9) Rinse the keratinous material with water,
wherein the sequence of steps (7), (8) and (9) is carried out at least twice.

In the context of a further form of execution, a procedure comprising the following steps in the order indicated is particularly preferred
(1) Application of agent (a) on the keratinous material,
(2) Allow the agent (a) to act for a period of from about 10 seconds to about 10 minutes, preferably from about 10 seconds to about 5 minutes,
(3) if necessary, rinse the keratinous material with water,
(4) Application of agent (b) on the keratinous material,
(5) Allow the agent (b) to act for a period of from about 30 seconds to about 30 minutes, preferably from about 30 seconds to about 10 minutes, and
(6) Rinse the keratinous material with water,
(7) Application of agent (c) on the keratinous material,
(8) allowing the agent (c) to act for a period of from about 30 seconds to about 10 minutes, preferably from about 30 seconds to about 50 minutes; and
(9) Rinse the keratinous material with water,
(10) Application of agent (c) on the keratinous material,
(11) allowing the agent (c) to act for a period of from about 30 seconds to about 10 minutes, preferably from about 30 seconds to about 50 minutes; and
(12) Rinse the keratinous material with water, In this embodiment, the sequence of steps (1) to (9) takes place within a few hours. There may be a period of a few days between carrying out steps (9) and (10). The sequence of steps (10) to (12) again takes place within a few hours.

Multi-Component Packaging Unit (Kit-of-Parts)

In the process as contemplated herein, agents (a), (b) and (c) are applied to the keratin materials, i.e., the three agents (a), (b) and (c) are respectively the ready-to-use agents.

To increase user comfort, the user is preferably provided with all required resources in the form of a multi-component packaging unit (kit-of-parts).

A second subject of the present disclosure is therefore a multi-component packaging unit (kit-of-parts) for coloring keratinous material, comprehensively packaged separately from one another
a first container comprising an agent (a), wherein the agent (a) comprises at least one organic silicon compound,
a second container comprising an agent (b), the agent (b) comprising at least one colorant compound selected from the group including pigments and/or direct dyes,
and a third container containing an agent (c), wherein the agent (c) contains at least one silicone oil.

The organic silicon compounds contained in agent (a) of the kit correspond to the organic silicon compounds that were also used in agent (a) of the method described above.

The colorant compounds from the group of pigments and/or direct dyes contained in agent (b) of the kit correspond to the colorant compounds from the group of pigments and/or direct dyes that were also used in agent (b) of the previously described process.

The silicone oils contained in agent (c) of the kit correspond to the silicone oils that were also used in agent (c) of the previously described process.

A second subject of the present disclosure is therefore a multi-component packaging unit (kit-of-parts) for coloring keratinous material, comprehensively packaged separately from one another
a first container comprising an agent (a), the agent (a) comprising at least one organic silicon compound as disclosed in detail in the description of the first subject matter of the present disclosure
a second container comprising an agent (b), the agent (b) comprising at least one colorant compound selected from the group including pigments and/or direct dyes, as disclosed in detail in the description of the first subject matter of the present disclosure
and a third container comprising an agent (c), wherein the agent (c) comprises at least one silicone oil as disclosed in detail when describing the first subject matter of the present disclosure.

The agent (a) contains with the organic silicon compound (s) a class of reactive compounds which can undergo hydrolysis or oligomerization and/or polymerization in the presence of water as described above. Due to their high reactivity, these organic silicon compounds form a film on the keratin material.

To avoid premature oligomerization or polymerization, it may be preferable to prepare ready-to-use agent (a) only shortly before use.

In the context of a further embodiment, a multi-component packaging unit (kit-of-parts) for coloring keratinic material is preferably packaged separately from one another
a first container comprising an agent (a1), wherein the agent (a1) comprises at least one organic silicon compound,
a second container containing an agent (a2), the agent (2) containing water, a third container comprising an agent (b), the agent (b) comprising at least one colorant compound selected from the group including pigments and/or direct dyes, and a fourth container containing an agent (c), wherein the agent (c) contains at least one silicone oil.

To provide a formulation that is as stable as possible during storage, the agent (a1) itself is preferably packaged with low or no water.

In a preferred embodiment, a multicomponent packaging unit (kit-of-parts) as contemplated herein the agent (a1)—based on the total weight of the agent (a1)—contains a water content of less than about 10% by weight, preferably less than about 5% by weight, more preferably less than about 1% by weight, even more preferably less than about 0.1% by weight and very particularly preferably less than about 0.01% by weight.

The agent (a2) contains water. In a preferred embodiment, a multi-component packaging unit (kit-of-parts) as contemplated herein the agent (a2)—based on the total weight of the agent (a2)—has a water content of from about 15 to about 100% by weight, preferably from about 35 to about 100% by weight, more preferably from about 55 to about 100% by weight, still more preferably from about 65 to about 100% by weight and very particularly preferably from about 75 to about 100% by weight.

Within this version, the ready-to-use agent (a) is now produced by mixing agents (a1) and (a2).

For example, the user can first mix or shake the agent (a1) containing the organic silicon compound(s) with the water-containing agent (a2). The user can now apply this mixture of (a1) and (a2) to the keratin materials—either directly after their production or after a short reaction time of 10 seconds to 20 minutes. Following this, the user can apply means (b) and (c) as previously described.

With respect to the other preferred embodiments of the multi-component packaging unit as contemplated herein, the same applies mutatis mutandis to the procedure as contemplated herein.

EXAMPLES

1. Formulations

The following formulations have been produced (unless otherwise indicated, all figures are in % by weight)

| Pretreatment agent, agent (a) | (a1) |
|---|---|
| (3-Aminopropyl)triethoxysilan | 2.0 |
| Methyltrimethoxysilane | 7.0 |
| Ammonia/citric acid | ad pH 9.5 |
| Water | ad 100 |

The silanes were mixed with a portion of water, this mixture was left for 30 minutes. Then the pH value was adjusted to the desired value by adding citric acid/ammonia. Water was then added to make up to 100 g.

| Dye, agent (b) | (b1) |
|---|---|
| Colorona Bronze (Merck, Mica, CI77491, Iron oxides, CI77019) | 1.0 |
| Unipure Red LC 3071 (Sensient, Aluminum hydroxide, CI 15850) | 1.0 |
| PVP K 30 (Ashland, ISP, Polyvinylpyrrolidone) | 4.5 |
| Dermacryl 79 (Akzo Nobel, Acrylates/Octylacrylamide Copolymer, CAS-Nr. 129702-02-9) | 4.5 |
| Ammonia (25% aqueous solution) | ad pH 10 |
| Water | ad 100 |

| After-treatment agent Agent (c) | (c1) | (c2) | (c3) | (c4) | (c5) |
|---|---|---|---|---|---|
| Cetearyl alcohol | 2.8 | 2.8 | 2.8 | 2.8 | 2.8 |
| Dehyquart A-CA (INCI: AQUA (WATER), CETRIMONIUM CHLORIDE) | 2.0 | 2.0 | 2.0 | 2.0 | 2.0 |
| Stearamidopropyldimethylamine | 1.0 | 1.0 | 1.0 | 1.0 | 1.0 |
| Citric acid, monohydrate | 1.4 | 1.4 | 1.4 | 1.4 | 1.4 |
| Dimethicone 5 cST (25° C.) (5 mm2/s, 25° C.) | — | 1.5 | — | — | — |
| Dimethicone 50 cST (25° C.) (50 mm2/s, 25° C.) | — | — | 1.5 | 3.0 | 4.5 |
| Water | ad 100 | ad 100 | ad 100 | ad 100 | ad 100 |

2. Application

One strand of hair (Kerling, Euronatural hair white) was dipped into the medium (a) and left in it for 1 minute. Afterwards, excess product (a) was stripped from each strand of hair. Each strand of hair was briefly washed with water. Excess water was scraped off each strand of hair.

Subsequently, the hair strands were each dipped in the agent (b) and left in it for 1 minute. Afterwards, excess agent (b) was stripped from each strand of hair. Each strand of hair was briefly washed with water. Excess water was scraped off each strand of hair.

After that, the hair strands were each wetted with a small amount of the agent (c). The agent (c) was left to act for 1 minute. Then washed out with water and dried the strand of hair. Afterwards the strands were visually evaluated. The feel of the dyed hair strands was also assessed by specially trained people.

| Specimen | 1 | 2 | 3 | 4 | 5 |
|---|---|---|---|---|---|
| Agent (a) | (a1) | (a1) | (a1) | (a1) | (a1) |
| Agent (b) | (b1) | (b1) | (b1) | (b1) | (b1) |
| Agent (c) | (c1) | (c2) | (c3) | (c4) | (c5) |
| Coloring | bronze red +++ | bronze red ++ | bronze red +++ | bronze red +++ | bronze red +++ |
| Hair feeling | heavily coated, oily, hair sticks together + | neat, minimally dry ++ | maintained, Minimal dry +++ | well-groomed, not oily, combs well +++ | neat, slightly occupied ++ |

Color intensity:
+ = bad
++ = average
+++ = excellent
Hair feeling:
+ = bad
++ = average
+++ = excellent While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for dyeing keratinous material comprising the steps of:
   applying an agent (a) to the keratinous material, wherein the agent (a) comprises at least one organic silicon compound,
   applying an agent (b) to the keratinous material, wherein the agent (b) comprises at least one colorant compound selected from the group of pigments and/or direct dyes,
   applying an agent (c) to the keratinous material, wherein the agent (c) comprises at least one silicone oil.

2. The process according to claim 1, wherein the agent (a) comprises the at least one organic silicon compound selected from silanes having one, two or three silicon atoms.

3. The process according to claim 1, wherein the agent (a) comprises the at least one organic silicon compound of the formula (I) and/or (II)

$$R_1R_2N\text{-}L\text{-}Si(OR_3)_a(R_4)_b \quad (I),$$

where
$R_1$, $R_2$ independently represent a hydrogen atom or a $C_1\text{-}C_6$ alkyl group,
L is a linear or branched divalent $C_1\text{-}C_{20}$ alkylene group,
$R_3$ is a hydrogen atom or a $C_1\text{-}C_6$ alkyl group,
$R_4$ represents a $C_1\text{-}C_6$ alkyl group,
a, stands for an integer from 1 to 3, and
b is the integer 3−a, and
wherein in the organic silicon compound of formula (II)

$$(R_5O)_c(R_6)_d Si\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II),$$

$R_5$, $R_5'$, $R_5''$ independently represent a hydrogen atom or a $C_1\text{-}C_6$ alkyl group,
$R_6$, $R_6'$ and $R_6''$ independently represent a $C_1\text{-}C_6$ alkyl group,
A, A', A", independently of one another represent a linear or branched divalent $C_1\text{-}C_{20}$ alkylene group
$R_7$ and $R_8$ independently represent a hydrogen atom, a $C_1\text{-}C_6$ alkyl group, a hydroxy $C_1\text{-}C_6$ alkyl group, a $C_2\text{-}C_6$ alkenyl group, an amino $C_1\text{-}C_6$ alkyl group or a group of formula (III)

$$\text{-}(A'''')\text{-}Si(R_6'')_{d''}(OR_5'')_{c''} \quad (III),$$

c, stands for an integer from 1 to 3,
d stands for the integer 3−c,
c' stands for an integer from 1 to 3,
d' stands for the integer 3−c',
c" stands for an integer from 1 to 3,
d" stands for the integer 3−c",
e stands for 0 or 1,
f stands for 0 or 1,
g stands for 0 or 1,
h stands for 0 or 1,
provided that at least one of e, f, g, and h is different from 0.

4. The process according to claim 1, wherein the agent (a) comprises the at least one organic silicon compound of formula (I), $$R_1R_2N\text{-}L\text{-}Si(OR_3)_a(R_4)_b \quad (I),$$

where
$R_1$, $R_2$ both represent a hydrogen atom, and
L represents a linear, divalent $C_1\text{-}C_6$-alkylene group,
$R_3$ represents a hydrogen atom, an ethyl group, or a methyl group,
$R_4$ represents a methyl group or an ethyl group,
a stands for the number 3 and
b stands for the number 0.

5. The process according to claim 1, wherein the agent (a) comprises the at least one organic silicon compound of formula (I) selected from the group of
   (3-Aminopropyl)triethoxysilan
   (3-Aminopropyl)trimethoxysilane
   1-(3-Aminopropyl)silantriol
   (2-Aminoethyl)triethoxysilan
   (2-Aminoethyl)trimethoxysilane
   1-(2-Aminoethyl)silantriol
   (3-Dimethylaminopropyl)triethoxysilan
   (3-Dimethylaminopropyl)trimethoxysilane
   1-(3-Dimethylaminopropyl)silantriol
   (2-Dimethylaminoethyl)triethoxysilan
   (2-Dimethylaminoethyl)trimethoxysilane and/or
   1-(2-Dimethylaminoethyl)silantriol.

6. The process according to claim 3, wherein the agent (a) comprises the at least one organic silicon compound of the formula (II), $$(R_5O)_c(R_6)_d Si\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II),$$

where
e and f both stand for the number 1,
g and h both stand for the number 0,
A and A' independently represent a linear, divalent $C_1\text{-}C_6$ alkylene group
and
$R_7$ represents a hydrogen atom, a methyl group, a 2-hydroxyethyl group, a 2-alkenyl group, a 2-aminoethyl group or a group of formula (III).

7. The process according to claim 3, wherein the agent (a) comprises the at least one organic silicon compound of the formula (II) which is selected from the group of
   3-(trimethoxysilyl)-N-[3-(trimethoxysilyl)propyl]-1-propanamine
   3-(Triethoxysilyl)-N-[3-(triethoxysilyl)propyl]-1-propanamine
   N-methyl-3-(trimethoxysilyl)-N-[3-(trimethoxysilyl)propyl]-1-propanamine
   N-Methyl-3-(triethoxysilyl)-N-[3-(triethoxysilyl)propyl]-1-propanamine
   2-[Bis[3-(trimethoxysilyl)propyl]amino]-ethanol
   2-[bis[3-(triethoxysilyl)propyl]amino]ethanol
   3-(Trimethoxysilyl)-N,N-bis[3-(trimethoxysilyl)propyl]-1-propanamine
   3-(Triethoxysilyl)-N,N-bis[3-(triethoxysilyl)propyl]-1-propanamine
   N1,N1-bis[3-(trimethoxysilyl)propyl]-1,2-ethanediamine,
   N1,N1-bis[3-(triethoxysilyl)propyl]-1,2-ethanediamine,
   N,N-bis[3-(trimethoxysilyl)propyl]-2-propen-1-amine and/or
   N,N-bis[3-(triethoxysilyl)propyl]-2-propen-1-amine.

8. The process according to claim 1, wherein the agent (a) comprises the at least one organic silicon compound of formula (IV)

$$R_9Si(OR_{10})_k(R_{11})_m \quad (IV),$$

where
R$_9$ represents a C$_1$-C$_{12}$ alkyl group,
R$_{10}$ represents a hydrogen atom or a C$_1$-C$_6$ alkyl group,
R$_{11}$ represents a C$_1$-C$_6$ alkyl group
k is an integer from 1 to 3, and
m stands for the integer 3-k.

9. The process according to claim 1, wherein the agent (a) comprises the at least one organic silicon compound of formula (IV) selected from the group of
Methyltrimethoxysilane
Methyltriethoxysilane
Ethyltrimethoxysilane
Ethyltriethoxysilane
Hexyltrimethoxysilane
Hexyltriethoxysilane
Octyltrimethoxysilane
Octyltriethoxysilane
Dodecyltrimethoxysilane and/or
Dodecyltriethoxysilane.

10. The process according to claim 1, wherein the agent (b) comprises the at least one coloring compound from the group of pigments selected from the group of colored metal oxides, metal hydroxides, metal oxide hydrates, silicates, metal sulfides, complex metal cyanides, metal sulphates, bronze pigments and/or from colored pigments based on mica or mica which are coated with at least one metal oxide and/or one metal oxychloride.

11. The process according to claim 1, wherein the agent (b) comprises the at least one coloring compound from the group of organic pigments selected from carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

12. The process according to claim 1, wherein the agent (b) comprises the at least one direct dye which is selected from the group of anionic, cationic, and nonionic direct dyes.

13. The process according to claim 12, wherein the agent (b) comprises the at least one anionic direct dye selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

14. The process according to claim 1, wherein the agent (c) comprises the at least one silicone oil having a viscosity of from about 5 to about 3000 mm2/s measured according to ASTM standard D-445.

15. The process according to claim 1, wherein the agent (c) comprises the at least one silicone oil from the group of polydimethylsiloxanes.

16. The process according to claim 1, wherein the agent (c) comprises—based on the total weight of the agent (c)—one or more silicone oils in a total amount of from about 0.1 to about 25.0% by weight.

17. The process according to claim 1, wherein first the agent (a) is applied, then the agent (b) is applied and subsequently the agent (c) is applied, wherein a period between the applications of the agents (a) and (c) does not exceed about 24 hours.

18. A method according to claim 1, comprising the following steps in the order indicated
(1) applying the agent (a) on the keratinous material,
(2) allowing the agent (a) to act for a period of from about 10 seconds to about 10 minutes,
(3) optionally rinsing the keratinous material with water,
(4) applying the agent (b) on the keratinous material,
(5) allowing the agent (b) to act for a period of from about 30 seconds to about 30 minutes,
(6) rinsing the keratinous material with water,
(7) applying the agent (c) on the keratinous material,
(8) allowing the agent (c) to act for a period of from about 30 seconds to about 10 minutes; and
(9) rinsing the keratinous material with water.

19. The process according to claim 1, further comprising the step of providing a kit-of-parts for dyeing keratinous material, the kit-of-parts comprising separately packaged:
a first container comprising the agent (a),
a second container comprising the agent (b),
and a third container comprising the agent (c).

* * * * *